(12) United States Patent
Khayrallah et al.

(10) Patent No.: US 8,741,950 B2
(45) Date of Patent: Jun. 3, 2014

(54) METHODS FOR TREATING OR PREVENTING FATIGUE

(75) Inventors: Moise A. Khayrallah, Morrisville, NC (US); Gary Bream, Cary, NC (US); Stephen E. Butts, Holly Springs, NC (US); Susan Marie Melnick, Parsippany, NJ (US); Duncan Taylor, Flemington, NJ (US)

(73) Assignee: SK Biopharmaceuticals Co., Ltd., Seoul (KR)

( * ) Notice: Subject to any disclaimer, the term of this patent is extended or adjusted under 35 U.S.C. 154(b) by 61 days.

(21) Appl. No.: 13/379,793

(22) PCT Filed: Jun. 21, 2010

(86) PCT No.: PCT/US2010/039313
§ 371 (c)(1),
(2), (4) Date: Dec. 21, 2011

(87) PCT Pub. No.: WO2011/005473
PCT Pub. Date: Jan. 13, 2011

(65) Prior Publication Data
US 2012/0142769 A1    Jun. 7, 2012

Related U.S. Application Data

(60) Provisional application No. 61/219,082, filed on Jun. 22, 2009.

(51) Int. Cl.
| | | |
|---|---|---|
| *A01N 47/10* | (2006.01) | |
| *A01N 33/02* | (2006.01) | |
| *A01N 33/18* | (2006.01) | |
| *A01N 33/24* | (2006.01) | |
| *A61K 31/27* | (2006.01) | |
| *A61K 31/135* | (2006.01) | |
| *A61K 31/04* | (2006.01) | |

(52) U.S. Cl.
USPC ........... 514/478; 514/489; 514/490; 514/646; 514/741

(58) Field of Classification Search
USPC .......................................... 514/478, 489, 490
See application file for complete search history.

(56) References Cited

U.S. PATENT DOCUMENTS

| | | |
|---|---|---|
| 5,756,817 A | 5/1998 | Choi et al. |
| 5,955,499 A | 9/1999 | Choi et al. |
| 6,140,532 A * | 10/2000 | Choi et al. ..................... 560/164 |
| 2008/0039529 A1 | 2/2008 | Sporn |
| 2009/0221553 A1 | 9/2009 | Palumbo et al. |
| 2009/0312416 A1 | 12/2009 | Ahnaou et al. |
| 2010/0331332 A1 | 12/2010 | Lee et al. |
| 2012/0004300 A1 | 1/2012 | Lee et al. |
| 2012/0004301 A1 | 1/2012 | Melnick et al. |

FOREIGN PATENT DOCUMENTS

| | | | | |
|---|---|---|---|---|
| WO | WO 98/15526 | * | 4/1998 | ............ C07C 271/12 |
| WO | WO 2006/133393 | * | 12/2006 | ........... A61K 31/165 |
| WO | WO 2011/055944 A2 | | 11/2010 | |
| WO | WO 2011/055965 A2 | | 11/2010 | |

OTHER PUBLICATIONS

Hasan et al., "How to Keep the Brain Awake? The Complex Molecular Pharmacogenetics of Wake Promotion," Neuropsychopharmacology 34:1625-1640 (2009).
Laino, "Narcolepsy Drug Fights Cancer Fatigue," WebMD Health News Jun. 4, 2008.
Neu et al., "Clinical complaints of daytime sleepiness and fatigue: how to distinguish and treat them, especially when they become 'excessive' or 'chronic'?," Acta Neurol. Belg. 110:15-25 (2010).

* cited by examiner

*Primary Examiner* — My-Chau T Tran
(74) *Attorney, Agent, or Firm* — Myers Bigel Sibley & Sajovec, P.A.

(57) ABSTRACT

The present invention relates to the use of compounds of the invention for treatment and/or prevention of fatigue, including fatigue associated with diseases or treatments.

15 Claims, 4 Drawing Sheets

METHODS FOR TREATING OR PREVENTING FATIGUE

RELATED APPLICATIONS

This application is a 35 U.S.C. §371 national phase application of PCT Application PCT/US2010/039313, filed Jun. 21, 2010, which claims priority to U.S. Provisional Application No. 61/219,082 filed Jun. 22, 2009. The entire content of each of these applications is incorporated herein by reference.

FIELD OF THE INVENTION

The present invention relates to the use of compounds of the invention for treatment and/or prevention of fatigue, including fatigue associated with diseases or treatments.

BACKGROUND OF THE INVENTION

Fatigue is a weariness or lack of energy that is generally not relieved by rest or sleep. Fatigue is a common side effect of many diseases and conditions, including depression, cancer, multiple sclerosis, Parkinson's disease, Alzheimer's disease, chronic fatigue syndrome, fibromyalgia, chronic pain, traumatic brain injury, AIDS, and osteoarthritis. Fatigue can also result from administration of some medications or therapies, such as chemotherapy, radiation therapy, bone marrow transplant, and anti-depressant medications. There have been few reports of effective treatments for fatigue.

The present invention provides improved methods for treating or preventing fatigue, e.g., fatigue associated with diseases or treatments.

SUMMARY OF THE INVENTION

The present invention provides methods of treating and/or preventing fatigue, e.g., fatigue associated with a disease and/or treatment, in a subject, comprising delivering to a subject in need thereof a treatment or prevention effective amount of a compound of formula I:

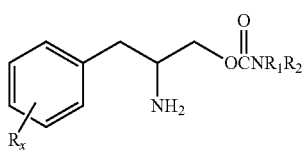

(I)

or a pharmaceutically acceptable salt or ester thereof, wherein
$R_x$ is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;
x is an integer of 1 to 3, with the proviso that R may be the same or different when x is 2 or 3;
$R_1$ and $R_2$ can be the same or different from each other and are independently selected from the group consisting of hydrogen, lower alkyl of 1 to 8 carbon atoms, aryl, arylalkyl, and cycloalkyl of 3 to 7 carbon atoms;
or $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

In one embodiment of the invention, the fatigue is associated with a particular disease, disorder, or condition, including without limitation, depression, cancer, multiple sclerosis, Parkinson's disease, Alzheimer's disease, chronic fatigue syndrome, fibromyalgia, chronic pain, traumatic brain injury, AIDS, and osteoarthritis. In another embodiment, the fatigue is associated with a particular treatment or therapy used to treat a disease, disorder, or condition, including without limitation, chemotherapy, radiation therapy, bone marrow transplant, and anti-depressant medications.

In another aspect of the invention, the compound of Formula I is administered concurrently with an additional agent or treatment, e.g., an agent or treatment for treating or preventing a disease, disorder, or condition.

The present invention is explained in greater detail in the drawings herein and the specification set forth below.

DETAILED DESCRIPTION OF THE INVENTION

Figure 1A:
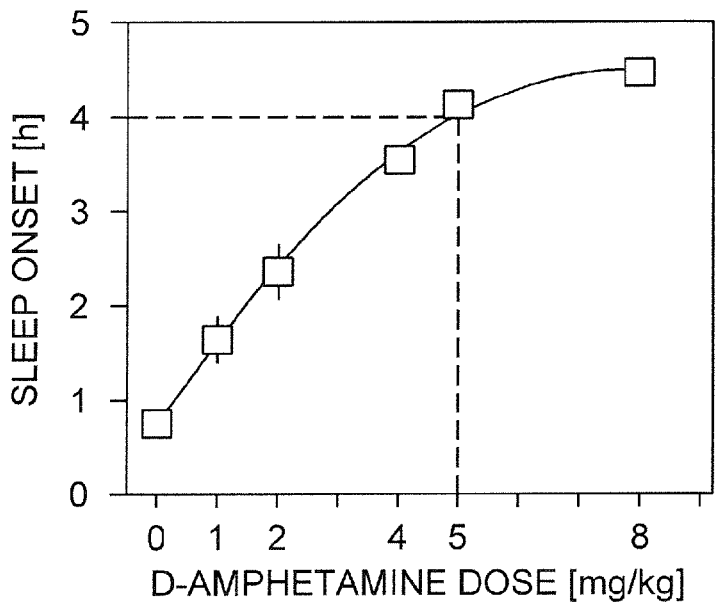
FIG. 1A shows sleep onset after repeated IP injections of d-amphetamine (A) at light onset (9:00 AM) in C57BL/6J mice.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

DEFINITIONS

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "treatment effective amount," as used herein, refers to that amount of a composition of this invention that imparts a modulating effect, which, for example, can be a beneficial effect, to a subject afflicted with a disorder, disease, or condition, including improvement in the condition of the subject (e.g., in one or more symptoms), delay or reduction in the progression of the condition, and/or change in clinical parameters, disease or condition, etc., as would be well known in the art. For example, a treatment effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The term "prevention effective amount," as used herein, refers to that amount of a composition of this invention that prevents or delays the onset of the disorder, disease, or condition (e.g., in one or more symptoms) or reduces the severity of the disorder, disease, or condition (e.g., in one or more symptoms) after onset, as would be well known in the art. For example, a prevention effective amount can refer to the amount of a composition, compound, or agent that delays onset of a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to the absence of administration.

"Treat" or "treating" or "treatment" refer to any type of action that imparts a modulating effect, which, for example, can be a beneficial effect, to a subject afflicted with a disorder, disease, or condition (e.g., fatigue), including improvement in the condition of the subject (e.g., in one or more symptoms), delay or reduction in the progression of the condition, and/or change in clinical parameters, disease or illness, etc., as would be well known in the art.

"Prevent" or "preventing" or "prevention" refer to prevention or delay of the onset of a disorder, disease, or condition (e.g., fatigue) and/or a decrease in the level of fatigue in a subject relative to the level of fatigue that would develop in the absence of the methods of the invention. The prevention can be complete, e.g., the total absence of fatigue in a subject. The prevention can also be partial, such that the occurrence of fatigue in a subject is less than that which would have occurred without the present invention.

Methods of assessing fatigue are known in the art and include psychometric scales such as the Fatigue Severity Scale, the HIV-Related Fatigue Scale, the Situational Fatigue Scale, the Fatigue Assessment Instrument, and the Functional Assessment of Chronic Illness Therapy-Fatigue.

The term "fatigue" is understood in the art and is generally defined as a condition characterized by a lessened capacity for work and reduced efficiency of accomplishment, usually accompanied by a feeling of weariness and tiredness as well as lack of mental sharpness, focus and concentration. Fatigue can either be acute or chronic. Fatigue is distinguished from sleepiness and disorders associated with sleepiness (such as excessive daytime sleepiness and narcolepsy). Fatigue is also distinguished from tiredness due to lack of adequate sleep.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 21$^{st}$ ed. 2005). Exemplary pharmaceutically acceptable carriers for the compositions of this invention include, but are not limited to, sterile pyrogen-free water and sterile pyrogen-free physiological saline solution.

The term "pharmaceutically acceptable salts or esters," as used herein, means nontoxic salts or esters of the compounds employed in this invention which are generally prepared by reacting the free acid with a suitable organic or inorganic base or the free base with a suitable organic or inorganic acid. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphateldiphosphate, polygalacturonate, potassium, salicylate, sodium, stearate, subacetate, succinate, tannate, tartrate, teoclate, tosylate, triethiodide, and valerate.

The term "a subject in need thereof," as used herein, refers to any subject or patient who currently has or may develop any of the above syndromes or disorders, including any condition or disorder which results in fatigue, or any other disorder in which the subject's present clinical condition or prognosis could benefit from the administration of one or more compounds of Formula I alone or in combination with another therapeutic intervention including but not limited to another medication.

The terms "fatigue associated with diseases or treatments" and "associated with fatigue" (and similar terms), as used herein, refer to any disease, disorder, condition, treatment, or medication that has fatigue as one of its symptoms or side effects.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The term "alkyl" denotes a straight or branched hydrocarbon chain containing 1-24 carbon atoms, e.g., 1-12 carbon atoms. The alkyl group can contain one or more double or triple bonds. Examples of alkyl group include methyl, ethyl, propyl, isopropyl, butyl, isobutyl, tert-butyl, and the like.

The term "cycloalkyl" refers to non-aromatic cyclic hydrocarbon moieties containing 3-24 carbon atoms, e.g., 3-12 carbon atoms. The cycloalkyl group can contain one or more double bonds. Examples include cyclopropyl, cyclobutyl, cyclopentyl, and cyclohexyl.

By "substituted alkyl" is meant an alkyl in which an atom of the alkyl is substituted with, for example, a carbon, nitrogen, sulfur, oxygen, silicon, or halogen atom, or alternatively a nitrogen, sulfur, oxygen, or halogen atom. The term encompasses substituents on alkyl, alkenyl, alkynyl, and cycloalkyl groups.

Examples of substituents that can be attached to any atom of the alkyl group in a "substituted alkyl" include cyclyl groups, heterocyclyl groups; aryl groups, heteroaryl groups, amino groups, amido groups, nitro groups, cyano groups, azide groups, hydroxy groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

The term "alkoxy" denotes an alkyl as defined above linked to an oxygen.

The term "thioalkoxy" denotes an alkyl as defined above linked to a sulfur.

The terms "halo" and "halogen" refer to any radical of fluorine, chlorine, bromine or iodine.

The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "aryl" refers to an aromatic 5-8 membered monocyclic, 8-12 membered bicyclic, or 11-14 membered tricyclic ring system wherein 0, 1, 2, or 3 atoms of each ring can be substituted by a substituent. Examples of aryl groups include phenyl, naphthyl and the like.

The term "heteroaryl" refers to an aromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "arylalkyl" denotes refers to an alkyl as defined above substituted with an aryl as defined above.

The term "heterocycle" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heterocyclyl groups include piperizinyl, pyrrolidinyl, dioxanyl, morpholinyl, tetrahydrofuranyl, and the like.

Suitable substituents for aryl, heteroaryl, and heterocycle groups are the same as the substituents for alkyl groups.

The present invention provides methods for treating and/or preventing fatigue in a subject, comprising delivering to a subject in need thereof, a treatment and/or prevention effective amount of a compound of Formula I:

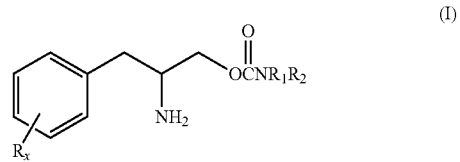

or a pharmaceutically acceptable salt or ester thereof, wherein $R_x$ is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, heteroaryl, arylalkyl, and cycloalkyl of 3 to 7 carbon atoms;

or $R_1$ and $R_2$ can be joined to form a 5 to 7-membered heterocycle substituted with a member selected from the group consisting of hydrogen, alkyl, aryl, and heteroaryl groups, wherein the cyclic compound can comprise 1 to 2 nitrogen atoms and 0 to 1 oxygen atom, wherein the nitrogen atoms are not directly connected with each other or with the oxygen atom.

In one embodiment, R is hydrogen and x=1. In another embodiment, R, $R_1$, and $R_2$ are all hydrogen and x=1. In a further embodiment, the compound has the structure:

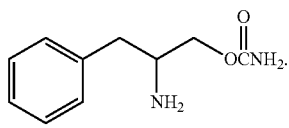

The compounds of Formula I can exist as enantiomers, e.g., R or S enantiomers. Thus, in one embodiment, the compound of Formula I is an enantiomer substantially free of other enantiomers or an enantiomeric mixture wherein one enantiomer of the compound predominates (enantiomeric excess). In one embodiment, one enantiomer predominates to the extent of at least about 60%, e.g., at least about 70%, 80%, 90%, 95%, 96%, 97%, 98%, or 99%. In one embodiment, the enantiomer is (R)-(beta-amino-benzenepropyl) carbamate or (O-carbamoyl-(D)-phenylalaninol) or an enantiomeric mixture wherein the enantiomer of (R)-(beta-amino-benzenepropyl) carbamate or (O-carbamoyl-(D)-phenylalaninol) predominates.

An isolated enantiomer is one that is substantially free of the corresponding enantiomer. Thus, an isolated enantiomer refers to a compound that is separated via separation techniques or prepared free of the corresponding enantiomer. The term "substantially free," as used herein, means that the compound is made up of a significantly greater proportion of one enantiomer, e.g., at least about 55, 60, 65, 70, 75, 80, 85, 90, 95, 96, 97, 98, or 99% of one enantiomer. Preferred enantiomers can be isolated from racemic mixtures by any method known to those skilled in the art, including high performance liquid chromatography (HPLC) and the formation and crystallization of chiral salts, or enantiomers can be prepared by methods described herein.

One compound of Formula I consists of the (D) enantiomer of the structure shown below wherein $R_x = R_1 = R_2 =$ hydrogen; in the structure shown below the amine group is directed down from the plane of the paper. This compound is the (R) enantiomer if named by structure and is therefore (R)-(beta-amino-benzenepropyl) carbamate. This compound is the dextrorotary enantiomer and can therefore also be named O-carbamoyl-(D)-phenylalaninol. The two chemical names may be used interchangeably in this specification. In one embodiment, the compound is in the form of a pharmaceutically acceptable salt, e.g., a hydrochloride salt.

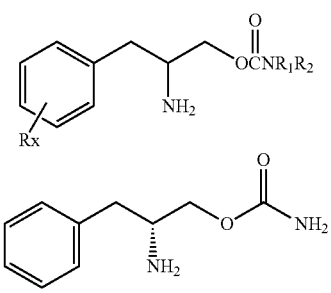

In one aspect of the invention, the fatigue is associated with a disorder, disease, or condition, e.g., depression, cancer, multiple sclerosis, Parkinson's disease, Alzheimer's disease, chronic fatigue syndrome, fibromyalgia, chronic pain, traumatic brain injury, AIDS, or osteoarthritis. In another embodiment, the fatigue is associated with a particular treatment or therapy used to treat and/or prevent a disease, disorder, or condition, including without limitation, chemotherapy, radiation therapy, bone marrow transplant, or antidepressant medications.

The compounds of Formula I can be synthesized by methods known to a skilled artisan. The salts and esters of the compounds of Formula I can be produced by treating the compound with a suitable mineral or organic acid (HX) in a suitable solvent or by other means well known to those of skill in the art.

Details of the above reaction schemes for synthesizing compounds of Formula I as well as representative examples of the preparation of specific compounds have been described in U.S. Pat. Nos. 5,705,640, 5,756,817, 5,955,499, and 6,140,532, all incorporated herein by reference in their entirety.

From Formula I it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

Similarly, compounds of the invention containing a double bond can exist in the form of geometric isomers, which can be readily separated and recovered by conventional procedures. Such isomeric forms are included in the scope of this invention.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999, The protecting groups may be removed at a convenient subsequent stage using methods known in the art.

Other embodiments of the invention include the use, for the preparation of a medicament for the treatment of fatigue, of one of the compounds or enantiomers or enantiomeric mixtures described above or a pharmaceutically acceptable salt or ester thereof.

The compounds of this invention include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynaphthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

Compounds of Formula I include those having quaternization of any basic nitrogen-containing group therein.

Further, the compounds of the invention include prodrugs of the compounds of Formula I that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. No. 6,680,324 and U.S. Pat. No. 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

In one embodiment of the invention, the compounds of the invention are administered to the subject as needed to treat and/or prevent fatigue. The compound can be administered continuously or intermittently. In one embodiment, the compound is administered to the subject multiple times a day, e.g. 2, 3, 4, or more times a day. In one embodiment, the compound is administered to the subject no more than once a day, e.g., once every 2, 3, 4, 5, or 6 days, once a week, e.g., no more than once every two weeks, once a month, once every two months, once every three months, once every four months, once every five months, once every six months, or longer. The compound can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more prior to the onset of fatigue (e.g., prior to an event that is likely to induce fatigue). The compound can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more after the onset of fatigue or an event likely to induce fatigue. In other embodiments, the compound can be administered by any discontinuous administration regimen. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject.

The compounds of the invention can be delivered to the subject by any suitable route, e.g., oral, rectal, buccal (e.g., sub-lingual), vaginal, parenteral (e.g., subcutaneous, intramuscular, intradermal, or intravenous), topical (i.e., both skin and mucosal surfaces, including airway surfaces) and transdermal administration. The compound is delivered to the subject at a dose that is effective to treat and/or prevent the fatigue. The effective dosage will depend on many factors including the gender, age, weight, and general physical condition of the subject, the severity of the fatigue, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of skill in the art by reference to the pertinent texts and literature and/or by using routine experimentation (see, e.g., Remington, *The Science and Practice of Pharmacy* (21$^{st}$ ed. 2005)). In one embodiment, the compound is administered at a dose of about 0.01 mg/kg/dose to about 300 mg/kg/dose, e.g., about 0.1 mg/kg/dose to about 200 mg/kg/dose, about 0.5 mg/kg/dose to about 100 mg/kg/dose, or about 0.01, 0.05, 0.1, 0.5, 1, 2, 3, 4, 5, 6, 7, 8, 9, 10, 15, 20, 25, 50, 75, 100, 125, 150, 175, 200, 225, 250, 275, or 300 mg/kg/dose. In some instances, the dose can be even lower, e.g., as low as 0.005 or 0.001 mg/m$^2$ or lower. In some instances, the dose can be even higher, e.g., as high as 500 or 1000 mg/kg/dose or higher. The present invention encompasses every sub-range within the cited ranges and amounts.

In one embodiment of the invention, the subject is one that has developed fatigue and the compound is administered to the subject after the development of fatigue. In another embodiment, the subject is one that has not developed fatigue and the compound is administered to the subject to prevent the occurrence of fatigue. In one embodiment, the subject is one that is undergoing an event that is likely to result in the development of fatigue. The compound can be delivered to the subject prior to the event occurring, concurrently with the event, and/or after the event occurs but before the development of fatigue. Events that are likely to result in the development of fatigue are well known and include, without limitation, diseases, disorders, or conditions such as depression, cancer, multiple sclerosis, Parkinson's disease, Alzheimer's disease, chronic fatigue syndrome, fibromyalgia, chronic pain, traumatic brain injury, AIDS, and osteoarthritis and medications or therapies such as chemotherapy, radiation therapy, bone marrow transplant, and anti-depressant medications. In one embodiment, the subject has depression. In another embodiment, the subject does not have depression.

In one aspect of the invention, the compound of the invention is delivered to a subject concurrently with an additional agent or treatment. The additional agent can be delivered in the same composition as the compound or in a separate composition. The additional agent or treatment can be delivered to the subject on a different schedule or by a different route as compared to the compound. The additional agent or treatment can be any agent or treatment that provides a benefit to the subject, e.g., as treatment and/or prevention for a disease, disorder, or condition that is associated with fatigue. Additional treatments include, without limitation, surgery, radiation therapy, and bone marrow transplantation. Additional agents include, without limitation, chemotherapeutic agents, antiemetic agents, analgesic agents (e.g., opioids and/or systemic local anesthetics), anti-inflammatory agents, antiviral agents, anti-depressant agents, and immunosuppressant agents.

Examples of chemotherapeutic agents include, without limitation, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfarnide, ilmofosine, interleukin II (including recombinant interleukin II or rIL2), interferon alfa-2a, interferon alfa-2b, interferon alfa-n1, interferon alfa-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, and zorubicin hydrochloride.

Examples of other chemotherapeutic agents include, but are not limited to, 20-epi-1,25 dihydroxyvitamin $D_3$; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; prostatic carcinoma antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansteron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stein cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of antiemetic agents include, without limitation, metoclopromide, domperidone, prochlorperazine, promethazine, chlorpromazine, trimethobenzamide, odansteron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of analgesic agents include, without limitation, the opioids allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, and tramadol.

Examples of anti-inflammatory agents include, without limitation, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, celecoxib, rofecoxib, and corticosteroids (e.g., prednisone, methylprednisolone, dexamethasone).

Examples of antiviral agents include, without limitation, hydroxyurea, ribavirin, IL-2, IL-12, pentafuside, 1-D-ribofuranosyl-1,2,4-triazole-3 carboxamide, 9-(2-hydroxyethoxy)methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Examples of anti-depressant agents include, without limitation, nefazodone, sertraline, trazodone, nortriptyne, amitriptine, imipramine, paroxetine, fluvoxamine, milnacipran, mirtazapine, mianserin, bupropion, lithium, nefazodone, trazodone, viloxazine, amitriptyline, clomipramine, and fluoxetine.

Examples of immunosuppressant agents include, without limitation, tacrolimus, sirolimus, cyclosporin, methotrexate, cyclophosphamide, azathioprine, mercaptopurine, and mycophenolate.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has fatigue and/or is anticipated to experience fatigue. In other embodiments, the subject used in the methods of the invention is an animal model of fatigue.

The compounds of the invention described above can be formulated for administration in a pharmaceutical carrier in accordance with known techniques. See, e.g., Remington, *The Science And Practice of Pharmacy* ($21^{st}$ ed. 2005). In the manufacture of a pharmaceutical formulation according to the invention, the compound is typically admixed with, inter alia, an acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation, for example, a tablet, which can contain from 0.01% or 0.5% to 95% or 99% by weight of the compound. One or more compounds can be incorporated in the formulations of the invention, which can be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the compound and a suitable carrier (which can contain one or more accessory ingredients as noted above). In general, the formulations of the invention are prepared by uniformly and intimately admixing the compound with a liquid or finely divided solid carrier, or both, and then, if necessary, shaping the resulting mixture. For example, a tablet can be prepared by compressing or molding a powder or granules containing the compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose (e.g., in a syringe or other injection device) or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described. For example, in one aspect of the present invention, there is provided an injectable, stable, sterile composition comprising one or more compounds, in a unit dosage form in a sealed container. The compound is provided in the form of a lyophilizate which is capable of being reconstituted with a suitable pharmaceutically acceptable carrier to form a liquid composition suitable for injection thereof into a subject. The unit dosage form typically comprises from about 1 μg to about 10 grams of the compound. When the compound is substantially water-insoluble (e.g., when conjugated to a lipid), a sufficient amount of emulsifying agent which is physiologically acceptable can be employed in sufficient quantity to emulsify the compound in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2 M active ingredient.

Other pharmaceutical compositions can be prepared from the compounds disclosed herein, such as aqueous base emulsions. In such an instance, the composition will contain a sufficient amount of pharmaceutically acceptable emulsifying agent to emulsify the desired amount of the compound. Particularly useful emulsifying agents include phosphatidyl cholines and lecithin.

In addition to compound, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA), viscomodulators, tonicifiers (e.g., a sugar such as sucrose, lactose, or mannitol), flavorants, colorants odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

The present invention is more particularly described in the following examples that are intended as illustrative only since numerous modifications and variations therein will be apparent to those skilled in the art.

EXAMPLE 1

The effects of (R)-(beta-amino-benzenepropyl) carbamate (also known as R228060, hereinafter referred to as test compound) at a dose of 50-150 mg/kg PO on various sleep parameters were evaluated in 8 hypocretin cell ablated narcoleptic mice (preproorexin/ataxin-3 transgenic) and their littermate wild-type mice, and the effects were compared with those of modafinil, a reference wake-promoting compound. The test compound showed significantly increased bouts of wakefulness in both wild-type and narcoleptic mice and was able to normalize sleep patterns of narcoleptic mice.

Methods

The polygraph signal (EEG and EMG) was captured with SleepSign (Kissei Comtech), and the sleep stage was visually scored with 10 sec epoch for wakefulness, non-REM sleep and REM sleep. Scoring criteria are: Wakefulness is characterized by desynchronized low-amplitude, mixed frequency (>4 Hz) EEG and high EMG activity. Rhythmic alpha (8-9 Hz) wave (with high EMG activities) may also appear. Non-REM is characterized by synchronized, high-amplitude, low-frequency (0.25-4 Hz) with reduced EMG activity (compared to wakefulness). EEG activity in REM sleep is similar to that in wakefulness, with desynchronized, mixed frequency low amplitude waves. Rhythmic alpha (8-9 Hz) wave with reduced EMG activities may also appear. EEG activity during REM sleep is reduced even further and in many cases, completely absent. Some muscle twitching may be apparent in the EMG trace during REM sleep.

Three drug doses of the test compound (50, 100 and 150 mg/kg PO) plus vehicle, were orally administered at ZT 2 (2 hours after light on) or ZT14 (2 hours after light off), and the effects on sleep were monitored for 6 hours after the drug administration (the sleep data was collected for 30 hours after the drug injection, and are available for further analysis). The doses for modafinil were 50 and 200 mg/kg PO (plus vehicle), and modafinil was also administered at ZT 2 and ZT14.

If the polygraph signals of some mice were not sufficient to score the sleep stage with accuracy (especially bad EMG), data from these animals were excluded, and the minimum of 5 animals (except for the highest dose of the test compound in wild-type mice in dark period, n=4) were included for the data analysis and number of animals were indicated in the figures.

Effects of test compound and modafinil on the amount of wake, non-REM sleep, REM sleep (cumulative seconds), number of episodes for each sleep stage during 6 hours, and mean wake/sleep-bout lengths (seconds) were analyzed in each animal and the mean of each parameter was calculated in each genotype. The effects of compounds on wake and sleep amounts are useful to evaluate the wake promoting potency, and the number of episodes for each sleep stage and the mean wake/sleep bout length are parameters for evaluating the sleep fragmentation. Amphetamine and modafinil, two main wake-promoting compounds currently used for the treatment of EDS associated with various etiologies (narcolepsy, idiopathic hypersomnia and secondary EDS), are known to increase wake time and prolong wake bout length in normal and EDS conditions.

With these data analyses, the wake-promoting and therapeutic effects of test compound in narcolepsy were evaluated, and the effects were compared with those of modafinil. A comparison of the effects between hypocretin deficient and wild-type mice is very useful in determining if the wake-promotion of the test compound is dependent on the availability of hypocretins, and if there is a possible change in the sensitivity of the receptive mechanisms of test compound in narcoleptic mice due to the hypocretin ligand deficiency.

Results

Effects on sleep during the resting period: Very potent wake-promoting effects of test compound in both wild-type and hypocretin-deficient narcoleptic mice were observed. The effects were dose-dependent, and administrations of 50, 100, and 150 mg/kg PO of test compound induced continuous wakefulness in most wild-type and narcoleptic mice for up to 3, 4 and 5 hours, respectively. During this period, Non-REM and REM sleep were completely suppressed. There were no abnormal EEG patterns after test compound administration, and sleep that occurred after the prolonged wakefulness was normal by polygraphic assessments.

In contrast, the wake promoting effects of modafinil were modest, and the wake promoting effect of 200 mg/kg of modafinil roughly corresponds to 50 mg/kg of test compound. However, modafinil did not strongly reduce REM sleep after the administration of 50 mg/kg of test compound. Furthermore, test compound potently reduced REM sleep, and this contrasts to the effects of modafinil.

Effects on Sleep During the Active Period:

The same experiment was repeated by administrating compounds in the active period. During the active period, narcoleptic mice spend more in sleep than wild-type mice. Wild-type animals typically stayed awake for almost three hours after vehicle administration. Similar to the effects observed during the light period, test compound dose-dependently increased wakefulness in both wild and narcoleptic mice. Wake-promoting effects in wild-type mice were, however, subtle during the dark period due to the high amount of wakefulness at the baseline, and only small effects were observed. In contrast, more pronounced wake-promoting effects were observed in narcoleptic mice, and wake amounts in these mice after 100 and 150 mg/kg test compound administration were brought up to the levels of wild-type mice, suggesting that this test compound normalizes the sleep/wake amount of narcoleptic mice. Similarly non-REM and REM sleep were reduced in narcoleptic mice by test compound and the amounts of non-REM and REM sleep were also brought down to the levels of wild-type mice. Similar but much weaker effects were also seen after modafinil administration in these mice. Although modafinil dose-dependently increased wakefulness in narcoleptic mice, the high dose of modafinil (200 mg/kg) did not bring the wake amount to that of the wild-type baseline levels.

EXAMPLE 2

The effects of test compound and d-amphetamine on vigilance states were examined in three mouse strains including C57BL/6J, AKR/J and DBA/2J. The test compound showed a genotype-independent increase in wakefulness and longer wakefulness compared to d-amphetamine.

Methods

At least 7 adult male mice of inbred strains C57BL/6J, AKR/J, and DBA/2J were recorded in 2 sessions of 72 continuous hours. The first 24 h in each session are considered as baseline followed the next day by the saline injection and the next day by 150 mg/kg of the test compound in the first session and 5 mg/kg d-amphetamine in the second session. The two sessions were separated by 7 days (wash-out period) and all injections were intraperitoneal (IP) and performed at light onset (9 am) in a volume of 5 ml/kg.

Results

Figure 1B:
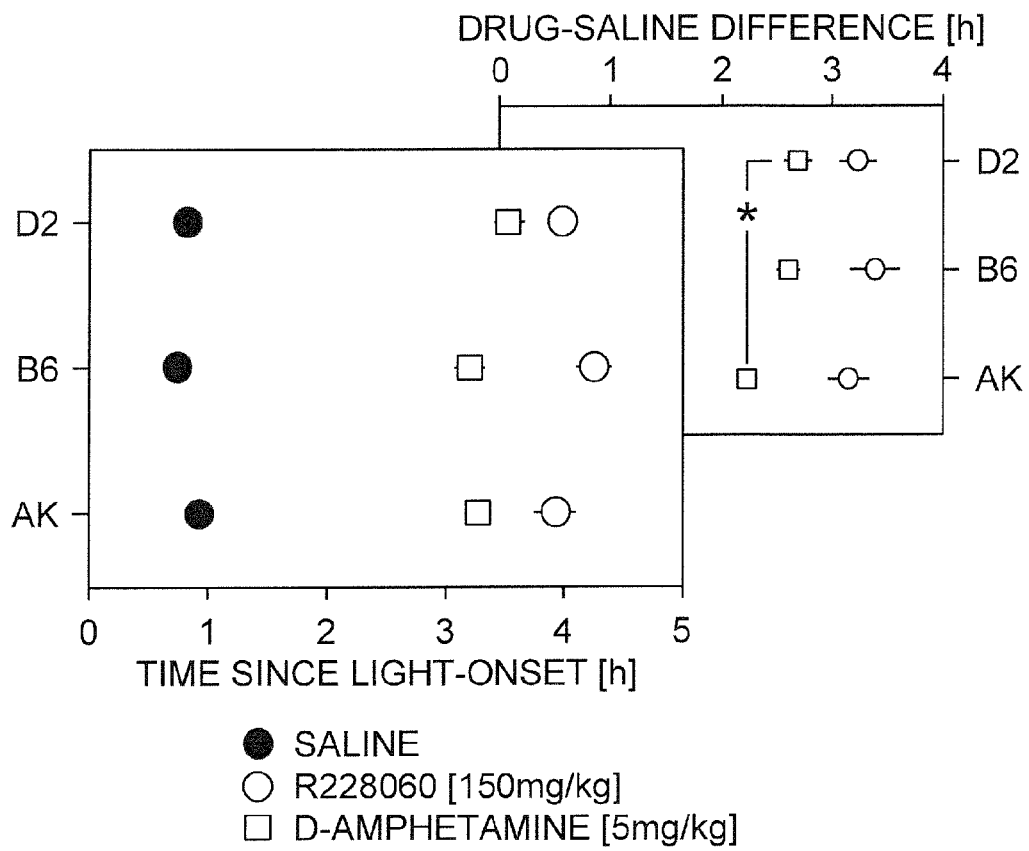
FIG. 1B shows sleep onset after a single IP injection of 150 mg/kg test compound (R228060) or 5 mg/kg d-amphetamine in three inbred strains of mice (D2=DBA/2J, B6=C57BL/6J, AK=AKR/J, n=7/strain). When expressed as a difference from the effect of a saline injection sleep onset after d-amphetamine differed between D2 and AK mice (asterisk; P<0.05; post-hoc Tukey) (see insert). Sleep onset under undisturbed baseline conditions (black symbols) are indicated for comparison. Error bars indicate ±1 SEM.

Dose-Response Effects of d-Amphetamine on Sleep Onset:

C57BL/6J mice were injected each day with 1, 2, 4, 5, and 8 mg/kg d-amphetamine and the sleep latencies calculated (FIG. 1A). D-amphetamine induced wakefulness in a dose-dependent manner between 1 and 5 mg/kg but there was no further increase in wakefulness amount at 8 mg/kg as compared to 5 mg/kg. Based on these data the dose of 5 mg/kg was chosen for the comparative experiment. FIG. 1B shows the sleep latencies after 5 mg/kg d-amphetamine as compared to 150 mg/kg of the test compound. The test compound at the dose of 150 mg/kg induced wakefulness for up to 4.5 continuous hours and wake time as referenced to sleep latency after the saline injection showed no genotype effect (FIG. 1B, insert). However and in contrast to the dose-response experiment (FIG. 1A), 5 mg/kg d-amphetamine failed to induce the same amount of wakefulness as 150 mg/kg of test compound. Interestingly, d-amphetamine induced less wakefulness in AK mice (long sleepers) than in D2 mice (short sleepers), suggesting a genotype-dependent effect of d-amphetamine (FIG. 1B, insert).

Figure 2:
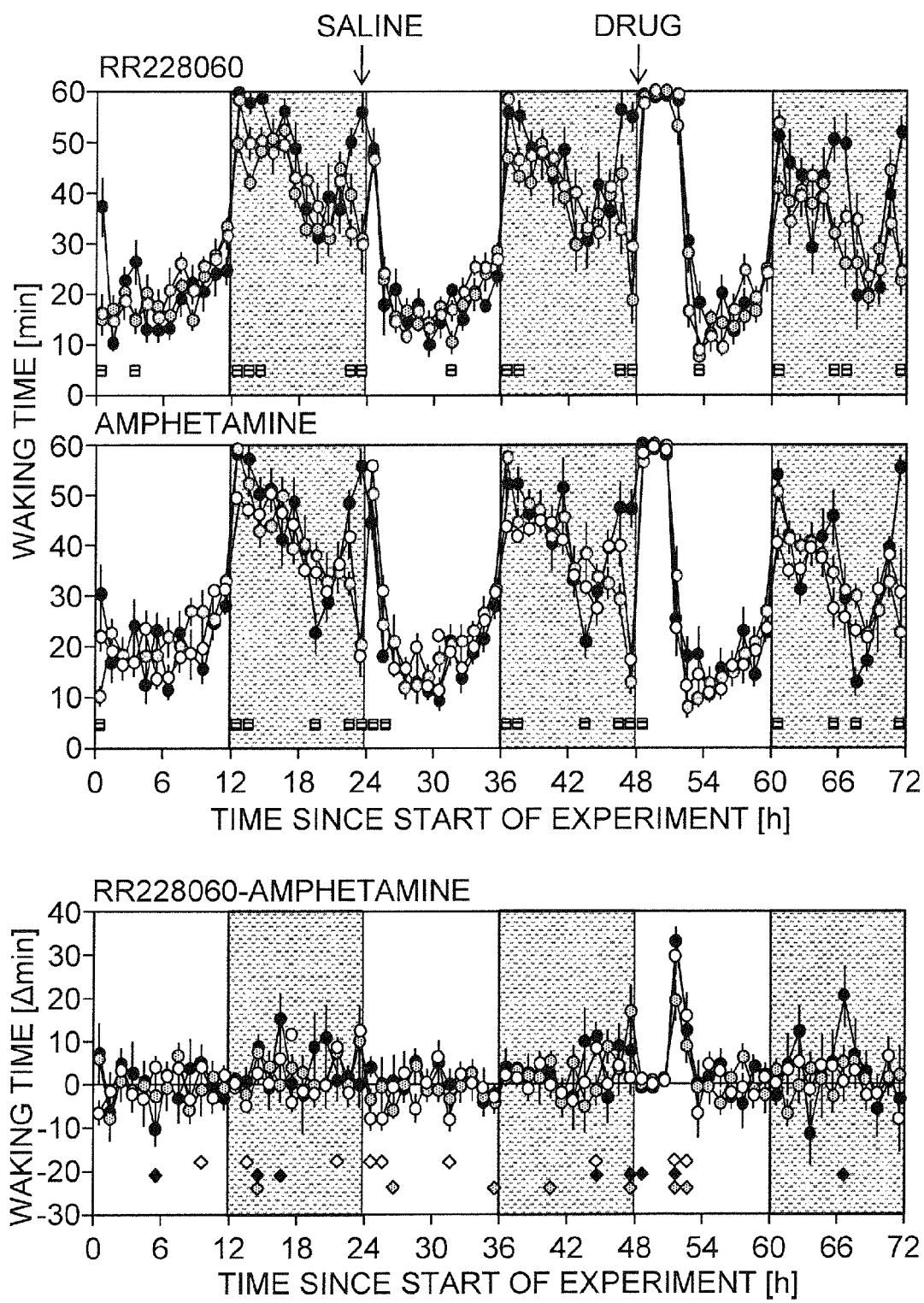
FIG. 2 depicts mean 1 h values of time spent awake for the 3 inbred strains (B6 black; D2 grey, and AK white symbols). Vertical bars represent ±1 SEM; (n=7/genotype). Grey areas mark the dark periods. Lower panel depicts differential effects of test compound (R228060) as compared to d-amphetamine. Dark-grey squares in upper and middle panels mark between genotype differences (1-way ANOVA; P<0.05). Diamonds in the lower panel mark significant differences between test compound and d-amphetamine paired t-tests; P<0.05; same color coding as in upper panel).

Effects on Vigilance States:

The hourly amounts of wakefulness throughout the 72 h recordings are depicted in FIG. 2. Although several significant between strain differences were noticed, test compound (upper panel) and d-amphetamine (middle panel) had very similar effects, except that the test compound induced significantly longer wakefulness duration than amphetamine (lower panel).

EXAMPLE 3

The sleep-wake organization in rats after acute administration of the test compound was examined. Treatment with the test compound at 30 mg/kg strongly increased active wakefulness at the expense of time spent in light sleep, deep sleep and REM sleep during the first 3 to 4 hours after the administration. Thus the test compound showed central activity immediately after injection as expressed in changes sleep-wake architecture in rats with a functional peak in effect around 2 hrs after i.p. administration.

Methods

The experiments were carried out on male adult Sprague Dawley rats, supplied by Harlan (Borchen, Germany) weighing 240-260 g at time of surgery. Animals were housed in full-view Plexiglas cages (25×33×18 cm) that fit to IVC-racks (individually ventilated cages) located in a sound-attenuated chamber. Rats were provided with a micro-chip for identification purposes and maintained under controlled environmental conditions throughout the study: 22±2° C. ambient temperature, relative humidity at 60%, 12:12 light-dark cycle (lights on from 12:00 hrs to 00:00 hrs; light intensity ~100 lux) with standard laboratory food chow and tap water available ad libitum.

Under isoflurane inhalation anesthesia, the rats were mounted in a stereotaxic apparatus. The oval area of the scalp was removed, and the uncovered skull was cleared of the periosteum. Three small cavities were drilled into the cranial bone without perforating the dura to receive 3 fixing stainless steel screws (diameter 1 mm) for polygraphic recording of frontal and parietal electroencephalogram (EEG). Two electrodes were placed stereotaxically on each side of the sagittal suture (AP+2 mm, L−2 mm; and AP−6 mm, L 3 mm from Bregma, while the third (reference) electrode was screwed over the cerebellum. The incisor bar was −5 mm under the centre of the ear bar. For the recording of the electro-oculogram (EOG) and electromyogram (EMG), stainless steel wires were placed in peri-orbital, and inserted into nuckal muscle, respectively. Electrodes (stainless steel wire, 7N51465T5TLT, 51/46 Teflon Bilaney, Germany) were connected to a pin (Future Electronics: 0672-2-15-15-30-27-10-0) with a small insert (track pins; Dataflex: TRP-1558-0000) were fitted into a 8 hole connector. Finally, the electrodes were fixed with dental cement to the cranium. The animals were housed individually and were allowed to recover for at least one week. Ten days after surgery, the animals were habituated for two weeks to the recording procedure in their home cages. The rats were connected at regular intervals with a cable to a rotating swivel allowing free movements while EEG, EOG and EMG activities were monitored.

Only rats that complied with the required criteria were used at time of testing, i.e., weight of animals 300-700 g, good polygraphical signal quality, a wash out period of at least 14 days in case of subject reuse, and no failure in two successive test sessions. For each compound, two EEG recording sessions were performed in 32 operated animals which were randomly assigned to 4 treatment conditions (n=8 rats per condition). The first recording session started at 14:00 hrs and lasted 16 hours after administration of saline (n=32 rats). The second recording session was performed for the same duration following administration of saline and different doses of test compound (1, 3 and 10 mg/kg), cocaine (3, 10 and 30 mg/kg i.p.), or amphetamine (3, 10, 30 mg/kg i.p.). All compounds were dissolved in saline and administered in a volume of 10 ml/kg body weight. An equivalent volume of saline was administered in control conditions.

Results

Figure 3:
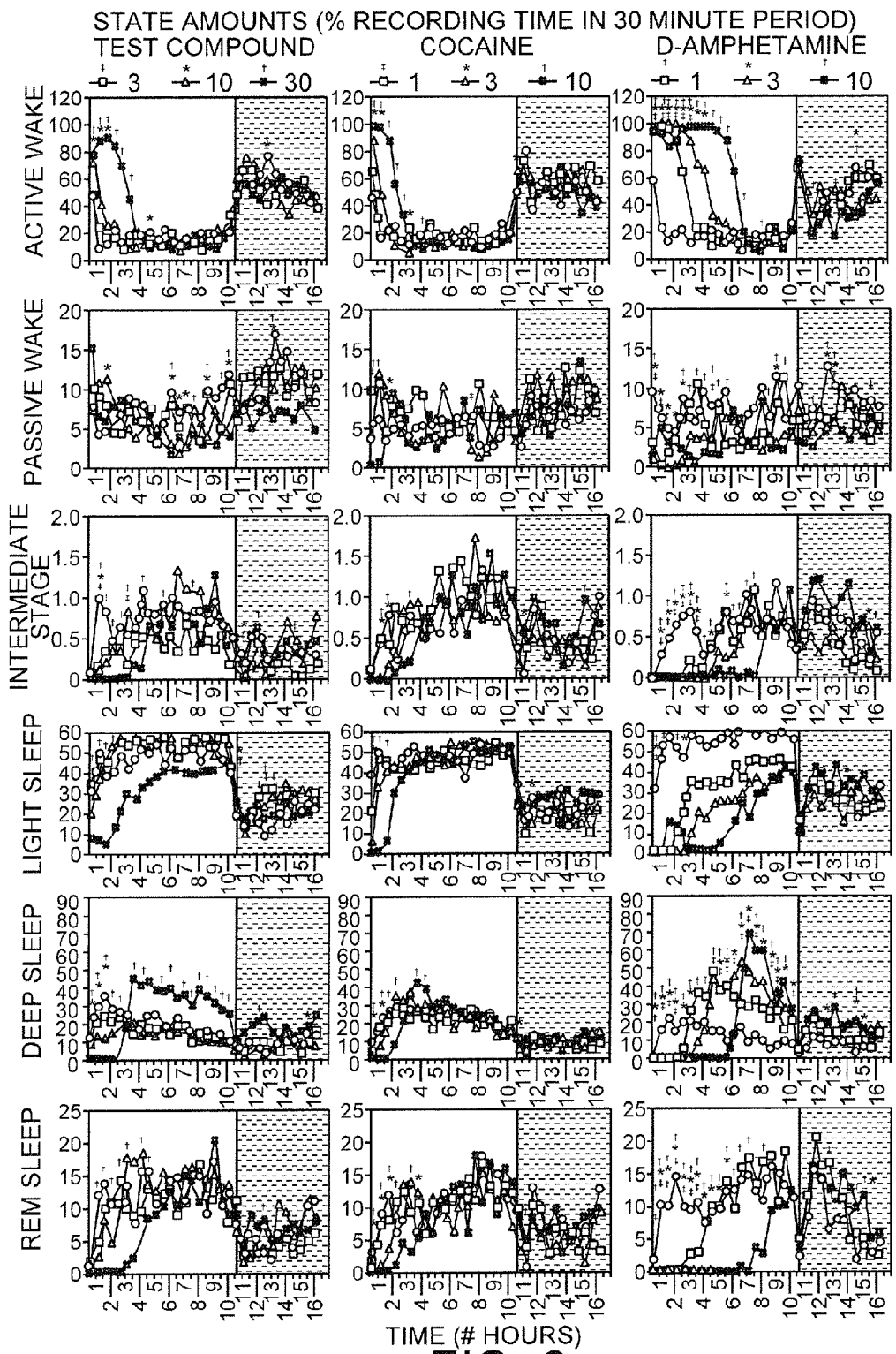
FIG. 3 shows the effects of test compound (3, 10, 30 mg/kg i.p.), cocaine (1, 3, 10 mg/kg i.p.), amphetamine (1, 3, 10 mg/kg i.p.) and vehicle (black circles) on sleep-wake states during sixteen consecutive hours following the administration.

The administration of test compound produced significant changes in the distribution of sleep-wake states (see FIG. 3, left panels). A slight modification of the sleep-wake architecture was observed throughout the 16 hours recording period following the administration of the lowest dose of the test compound (3 mg/kg i.p.). An increase in total light sleep (+26%, $p<0.05$) and an increased drive to wakefulness from light sleep as well as deep sleep (+46%, p<0.001; +15%, p<0.05; respectively) were observed indicating aspects of sleep fragmentation following this dose of the test compound (p<0.05) (see Table 1).

TABLE 1

|  | Dose | Latency (min) | | |
|---|---|---|---|---|
|  |  | lSWS | dSWS | REM sleep |
| Vehicle (i.p.) |  | 14.2 ± 2.1 | 38.2 ± 15.0 | 50.5 ± 8.5 |
| Test Comp. (mg/kg i.p.) | 3 | 15.6 ± 4.1 | 42.0 ± 8.5 | 66.0 ± 11.8 |
| Test Comp. (mg/kg i.p.) | 10 | 30.4 ± 7.9 | 127.2 ± 67.1 | 87.5 ± 14.5* |
| Test Comp. (mg/kg i.p.) | 30 | 73.6 ± 25.7 | 174.6 ± 12.3* | 251.8 ± 32.0* |
| Vehicle (i.p.) |  | 18.6 ± 5.8 | 27.5 ± 8.4 | 39.0 ± 5.6 |
| Cocaine (mg/kg i.p.) | 1 | 69.9 ± 51.2 | 79.3 ± 26.7 | 74.3 ± 12.1* |
| Cocaine (mg/kg i.p.) | 3 | 41.5 ± 9.2* | 68.6 ± 7.6* | 112.0 ± 12.2* |
| Cocaine (mg/kg i.p.) | 10 | 101.8 ± 6.9* | 138.8 ± 8.7* | 192.1 ± 18.5* |
| Vehicle (i.p.) |  | 16.1 ± 3.5 | 62.3 ± 11.5 | 93.4 ± 37.0 |

TABLE 1-continued

|  | Dose | Latency (min) | | |
|---|---|---|---|---|
|  |  | lSWS | dSWS | REM sleep |
| Amphetamine (mg/kg i.p.) | 1 | 140.6 ± 13.4* | 161.7 ± 5.3* | 208.6 ± 14.4* |
| Amphetamine (mg/kg i.p.) | 3 | 228.2 ± 25.0 | 242.0 ± 19.4* | 338.6 ± 24.3* |
| Amphetamine (mg/kg i.p.) | 10 | 284.7 ± 56.1* | 367.3 ± 5.5* | 440.8 ± 57.8* |

Values are means ± s.e.m of 8 rats.
*p < 0.05: Wilcoxon-Mann-Whitney rank sum tests indicate statistical significance between drug and vehicle.

At the dose of 10 mg/kg i.p., test compound produced changes in the sleep wake organization associated with a significant increase in total duration of light sleep (+24%, p<0.05) and a significant increase in shifts from REM sleep towards active wakefulness (+16%, p<0.05) (see Tables 2 and 3). During the first 90 minutes of the recording period a significant decrease in deep sleep duration in favor of increase in time spent in active wakefulness was observed (see FIG. 3, left panels) (p<0.05).

TABLE 2

|  | Dose | Duration (min) | | | | | |
|---|---|---|---|---|---|---|---|
|  |  | Active wake | Passive wake | Intermediate stage | Light sleep | Deep sleep | REM sleep |
| Vehicle (i.p.) |  | 313.0 ± 17.2 | 80.5 ± 8.0 | 5.1 ± 1.0 | 295.7 ± 21.5 | 152.7 ± 24.3 | 96.4 ± 4.5 |
| Test Comp. (mg/kg i.p.) | 3 | 290.0 ± 11.2 | 79.5 ± 10.7 | 2.9 ± 0.7* | 374.7 ± 16.6* | 125.0 ± 24.6 | 84.0 ± 5.4 |
| Test Comp. (mg/kg i.p.) | 10 | 305.5 ± 15.1 | 73.4 ± 13.2 | 5.2 ± 0.7 | 366.6 ± 21.2* | 104.0 ± 19.3 | 102.3 ± 4.6 |
| Test Comp. (mg/kg i.p.) | 30 | 371.6 ± 7.7* | 57.3 ± 4.7* | 4.0 ± 1.0 | 235.8 ± 14.3* | 214.9 ± 15.6 | 72.9 ± 7.3* |
| Vehicle (i.p.) |  | 304.3 ± 27.5 | 54.1 ± 11.5 | 5.9 ± 1.0 | 317.1 ± 26.3 | 181.4 ± 20.1 | 91.2 ± 5.1 |
| Cocaine (mg/kg i.p.) | 1 | 331.5 ± 41.5 | 69.8 ± 11.0 | 6.7 ± 1.0 | 293.2 ± 26.3 | 162.9 ± 26.3 | 84.2 ± 8.1 |
| Cocaine (mg/kg i.p.) | 3 | 324.8 ± 18.3 | 66.7 ± 8.9 | 5.7 ± 0.6 | 303.2 ± 42.5 | 172.6 ± 34.3 | 76.7 ± 6.3 |
| Cocaine (mg/kg i.p.) | 10 | 347.3 ± 16.5 | 55.0 ± 10.4 | 6.3 ± 1.1 | 294.6 ± 24.4 | 171.9 ± 23.8 | 74.7 ± 7.5 |
| Vehicle (i.p.) |  | 301.0 ± 18.7 | 74.4 ± 12.0 | 5.7 ± 1.0 | 371.7 ± 20.6 | 108.9 ± 23.7 | 91.5 ± 7.8 |
| Amphetamine (mg/kg i.p.) | 1 | 382.4 ± 19.6* | 50.0 ± 19.6* | 4.0 ± 19.6* | 242.7 ± 19.6* | 188.0 ± 19.6* | 88.6 ± 19.6 |
| Amphetamine (mg/kg i.p.) | 3 | 441.8 ± 15.7* | 43.5 ± 4.4* | 4.0 ± 1.0* | 187.9 ± 23.9* | 207.6 ± 17.7* | 71.4 ± 4.1* |
| Amphetamine (mg/kg i.p.) | 10 | 498.7 ± 19.0* | 35.6 ± 4.7* | 4.0 ± 1.0* | 182.0 ± 26.3* | 181.2 ± 22.0* | 53.6 ± 5.0* |

Values are means ± s.e.m of 8 rats.
*p < 0.05: Wilcoxon-Mann-Whitney rank sum tests indicate statistical significance of the vehicle-drug comparisons

TABLE 3

|  | Dose | Shifts (number) | | | | | |
|---|---|---|---|---|---|---|---|
|  |  | Shift from lSWS to | | Shift from dSWS to | | Shift from REMS to | |
|  |  | AW | PW | AW | PW | AW | PW |
| Vehicle (i.p.) |  | 148.6 ± 33.1 | 115.1 ± 45.0 | 9.1 ± 6.2 | 39.1 ± 24.1 | 81.7 ± 23.1 | 8.1 ± 5.4 |
| Test Comp. (mg/kg i.p.) | 3 | 217.8 ± 55.5* | 78.1 ± 35.8 | 9.7 ± 6.6* | 6.6 ± 5.9* | 78.0 ± 21.6 | 3.7 ± 3.0 |
| Test Comp. (mg/kg i.p.) | 10 | 204.5 ± 56.4 | 84.4 ± 40.5 | 4.2 ± 3.1 | 12.5 ± 8.5 | 94.1 ± 24.0 | 8.9 ± 6.7 |
| Test Comp. (mg/kg i.p.) | 30 | 221.9 ± 58.3* | 74.2 ± 29.0* | 8.7 ± 5.3 | 17.6 ± 12.0 | 65.1 ± 21.8* | 4.1 ± 3.2* |
| Vehicle (i.p.) |  | 228.1 ± 56.3 | 114.5 ± 48.3 | 10.6 ± 6.5 | 45.2 ± 28.1 | 77.5 ± 21.9 | 13.2 ± 7.7 |
| Cocaine (mg/kg i.p.) | 1 | 184.1 ± 48.1 | 128.6 ± 45.2 | 10.1 ± 5.6 | 66.6 ± 48.2 | 74.5 ± 21.5 | 17.0 ± 8.8 |

TABLE 3-continued

| | | Shifts (number) | | | | | |
| --- | --- | --- | --- | --- | --- | --- | --- |
| | | Shift from lSWS to | | Shift from dSWS to | | Shift from REMS to | |
| | Dose | AW | PW | AW | PW | AW | PW |
| Cocaine (mg/kg i.p.) | 3 | 218.5 ± 50.6 | 142.2 ± 48.5 | 10.2 ± 6.7 | 64.5 ± 42.6 | 56.0 ± 16.4 | 10.7 ± 6.9 |
| Cocaine (mg/kg i.p.) | 10 | 201.2 ± 53.6 | 132.6 ± 48.2 | 10.4 ± 6.2 | 37.6 ± 23.8 | 52.3 ± 16.5 | 9.2 ± 5.8 |
| Vehicle (i.p.) | | 204.0 ± 45.7 | 79.6 ± 40.1 | 9.1 ± 5.5 | 10.2 ± 8.9 | 74.2 ± 20.6 | 6.1 ± 4.3 |
| Amphetamine (mg/kg i.p.) | 1 | 198.8 ± 50.1 | 64.4 ± 30.5 | 11.7 ± 7.2 | 37.7 ± 30.0 | 66.5 ± 19.1 | 5.8 ± 4.8 |
| Amphetamine (mg/kg i.p.) | 3 | 178.7 ± 46.6 | 62.4 ± 26.1 | 14.8 ± 7.8 | 26.6 ± 16.8 | 59.3 ± 17.8 | 3.3 ± 2.6 |
| Amphetamine (mg/kg i.p.) | 10 | 201.7 ± 66.1 | 49.0 ± 25.5 | 9.7 ± 5.9 | 11.6 ± 8.9 | 50.0 ± 16.2* | 2.2 ± 1.9* |

Values are means ± s.e.m of 8 rats.
*p < 0.05: Wilcoxon-Mann-Whitney rank sum tests indicate statistical significance of the vehicle-drug comparisons.

At the highest dose (30 mg/kg i.p.) the test compound produced pronounced changes in the distribution of the sleep-wake cycle (see FIG. 3). Changes included a marked increase of the total time spent in the active wakefulness (+19%, p<0.05), a reduction of total time spent in passive wakefulness (−29%, p<0.05), in light sleep (−20%, p<0.05) as well as REM sleep (−25%, p<0.05) over the course of the 16-h post-injection period of the registration (see Table 2). In addition, when compared to total sleep time, test compound induced an increase in time spent in deep sleep and decreased time in REM sleep (p<0.05) (see Table 3).

A significant enhancement of active wakefulness was observed during the first 3 hours following the administration of the test compound (p<0.01). Concomitantly, a large reduction in the time spent in sleep e.g., light sleep (p<0.01), deep sleep (p<0.01) and REM sleep (p<0.01) was observed, followed by a rebound effect, particularly an increase in deep sleep after 3 hours following the administration of the test compound. The latter effect lasted about 7 hours during the light period of the recording (see FIG. 1). It should be noted that the onset of activity of the test compound was almost immediate, namely around the first 30 minutes following administration.

The large increase in total time spent in active wakefulness and the reduction in passive wakefulness, light sleep and REM sleep were due to an increase (+19%, p<0.05), and a decrease (−30%, p<0.05; −23%, p<0.05; −24%, p<0.01) in the number of epochs of these sleep-wake stages, respectively. However, the mean durations of these sleep wake states were not modified.

As depicted (see Table 3), the test compound at 30 mg/kg produced an increase in the number of shifts from light sleep and REM sleep towards wakefulness (p<0.05) and thus suggests indications of sleep fragmentation. Examination of sleep latencies revealed significant changes following test compound administration (see Table 1). Test compound at 10 and 30 mg/kg produced a significant lengthening of the latencies of REM sleep onset.

The present findings show that almost immediately after intraperitoneal injection test compound was centrally active for at least 4 hours with a peak in effect around 2 hours post administration. Only minor effects on sleep-wake architecture were observed at the lowest dose tested of 3 mg/kg. Changes in the sleep parameters were observed with the middle (10 mg/kg) and more specifically with the higher dose of 30 mg/kg tested. The modifications of the sleep-wake distribution which were most obvious during the first 3 hours of the registration period were characterized by a large increase of time spent in active wakefulness, while time spent in passive wakefulness, light sleep, deep sleep and REM sleep was reduced. Interestingly, test compound produced a rebound effect of recovery deep sleep associated with a marked increase in time spent in this state up to 7 hours.

The effects observed in this comparative study clearly suggest that the test compound at 30 mg/kg has psychostimulant-like properties at the beginning of the administration while a consequently following increase in sleep propensity as shown by deep sleep enhancement points towards a potential indirect effect on sleep homeostasis. The overall test compound profile of effects at 30 mg/kg was remarkably similar to the profile observed following the administration of amphetamine at the lowest dose tested of 1 mg/kg, both in terms of effect pattern, size and duration.

EXAMPLE 4

The primary objective of this study was to determine the efficacy of 2 target doses of test compound (200 and 400 mg/day) in comparison with placebo during 6 weeks of treatment in adult human subjects with moderate or severe major depression without psychotic features. An active comparator (paroxetine) was included to assist in distinguishing a negative study from a failed study. In addition, an exit interview was intended to gather information on unexpected benefits of the test compound in order to refine the clinical development program. One or both doses of the test compound demonstrated statistically significantly greater efficacy than placebo on a broad array of secondary efficacy variables of mood and well-being, suggesting antidepressant activity for the test compound. In addition, positive effects of the test compound on ratings of physical energy/fitness, reduction in sadness or depression and mental energy or motivation.

Methods

This was a randomized, double-blind, parallel-group, active, and placebo-controlled, multicenter study conducted in the U.S. (23 centers) and Canada (4 centers). There were 2 phases: a pretreatment phase (screening/washout and a baseline visit) and a 6-week, double-blind treatment phase. Paroxetine, a positive control, was included to evaluate assay sensitivity. After washout (if needed) of prohibited substances, subjects were randomly assigned (1:1:1:1) to receive the test compound titrated to a target dose of 200 mg/day or 400 mg/day, matching placebo, or a fixed dose (20 mg/day) of paroxetine. Study drug was given twice daily for 6 weeks, Efficacy and safety were assessed weekly during the double-blind phase. Subjects completing the study underwent an Exit Interview ("Your Health and Well-Being") and completed an Assessment of Benefits of Clinical-trial Drug-treatment (ABCD) questionnaire (U.S. sites only).

Results

Figure 4:
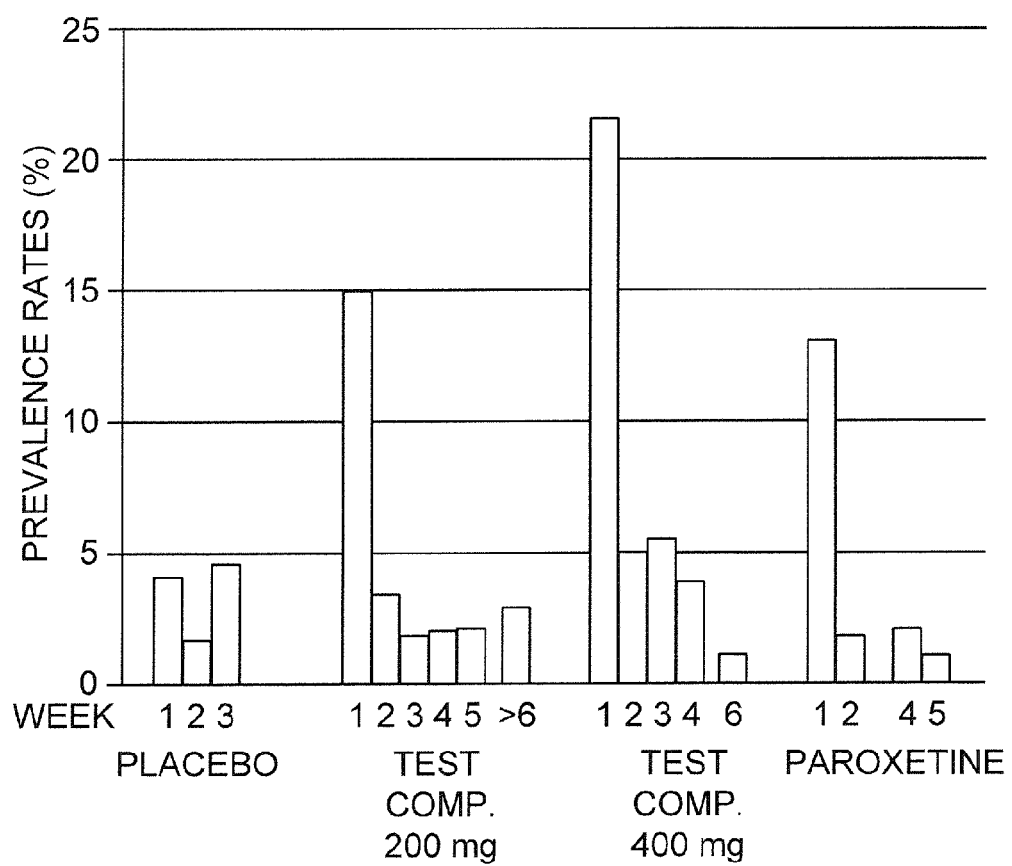
FIG. 4 shows the prevalence of insomnia by treatment group and week.

Insomnia was the most common treatment-emergent adverse event in the test compound groups (200 mg: 24%; 400 mg: 35%), compared with 10% in the placebo group and 17% in the paroxetine group, but it did not result in many discontinuations or appreciable rescue medication use. FIG. 4 presents the prevalence of insomnia by treatment group and week. Insomnia in the test compound groups, as well as in the paroxetine group, was most prevalent during the first week. The duration of insomnia was generally similar across the treatment groups.

Results from the U.S. sites of the Exit Interview and the self-rated and blinded ABCD questionnaire on the benefits of treatment in the study provided a context for interpreting the results of TC-MDD-201 from the subject's perspective. The exit interview data indicated that positive experiences most frequently included improvements in mood and well-being in all 4 treatment groups. This was supported by data from the ABCD questionnaire, in which the most improved aspect of health during the trial was "reduction in sadness and depression". Mood, generally speaking, was the first symptom to improve, with improvement noticed mostly within the first three weeks of receiving study medication (Exit Interview data).

In general, there were few differences between the 4 treatment groups within the 51 items on the ABCD questionnaire. Those that were apparent were generally most robust between placebo and the active medications (i.e., "physical energy/fitness", "reduction in sadness or depression" and "mental energy or motivation") rather than between the active medications themselves. In post hoc analyses, statistically significant superiority to placebo was observed for test compound 200 mg, test compound 400 mg, and paroxetine on 14, 8, and 14 items, respectively, of the questionnaire. However, there were no statistically significant differences between test compound 400 mg and test compound 200 mg, or between paroxetine and test compound (combined scores for both doses) for any of the 51 items on the ABCD questionnaire.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A method for treating or preventing fatigue in a subject, comprising administering to a subject in need thereof, a treatment or prevention effective amount of a compound of Formula I:

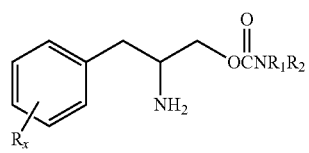

or a pharmaceutically acceptable salt, ester, or prodrug thereof, wherein $R_x$ is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, heteroaryl, arylalkyl, and cycloalkyl of 3 to 7 carbon atoms;

or $R_1$ and $R_2$ can be joined to form a 5 to 7-membered heterocycle substituted with a member selected from the group consisting of hydrogen, alkyl, aryl, and heteroaryl groups, wherein the cyclic compound can comprise 1 to 2 nitrogen atoms and 0 to 1 oxygen atom, wherein the nitrogen atoms are not directly connected with each other or with the oxygen atom.

2. The method of claim 1, wherein R is hydrogen and x=1.

3. The method of claim 1, wherein R, $R_1$, and $R_2$ are all hydrogen and x=1.

4. The method of claim 1, wherein the compound of Formula I is:

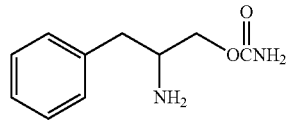

or a pharmaceutically acceptable salt, ester, or prodrug thereof.

5. The method of claim 1, wherein the compound of Formula I is an enantiomer substantially free of other enantiomers or an enantiomeric mixture wherein one enantiomer of the compound predominates.

6. The method of claim 5, wherein one enantiomer predominates to the extent of at least about 90%.

7. The method of claim 5, wherein one enantiomer predominates to the extent of at least about 98%.

8. The method of claim 5, wherein the compound is

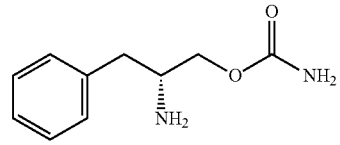 [SMILES: NC(=O)OC[C@H](N)Cc1ccccc1]

or a pharmaceutically acceptable salt, ester, or prodrug thereof.

9. The method of claim 1, wherein the fatigue is associated with a disease, disorder or condition.

10. The method of claim 9, wherein the disease, disorder or condition is selected from the group consisting of depression, cancer, multiple sclerosis, Parkinson's disease, Alzheimer's disease, chronic fatigue syndrome, fibromyalgia, chronic pain, traumatic brain injury, AIDS, and osteoarthritis.

11. The method of claim 1, wherein the fatigue is associated with a treatment or medication.

12. The method of claim 11, wherein the treatment or medication is selected from the group consisting of chemotherapy, radiation therapy, bone marrow transplant, and antidepressant treatment.

13. The method of claim 1, wherein the compound is administered concurrently with an additional agent or treatment.

14. The method of claim 1, wherein the compound is administered prior to an event that may result in fatigue, concurrently with an event that may result in fatigue, and/or after the onset of fatigue.

15. The method of claim 1, wherein the treatment or prevention effective amount of the compound is from about 0.01 mg/kg/dose to about 300 mg/kg/dose.

* * * * *